United States Patent [19]

Akhtar et al.

[11] Patent Number: 5,432,163

[45] Date of Patent: Jul. 11, 1995

[54] ANTI-PROLIFERATIVE AND ANTI-INFLAMMATORY COMPOUNDS: DERIVATIVES OF PENTOSE MONOSACCHARIDES

[75] Inventors: M. Nayeem Akhtar, Lansdale; David S. Thomson, Bluebell; Sudershak K. Arora, Lansdale, all of Pa.

[73] Assignee: Greenwich Pharmaceuticals Incorporated, Ft. Washington, Pa.

[21] Appl. No.: 975,700

[22] Filed: Nov. 13, 1992

[51] Int. Cl.⁶ .................. A61K 31/70; C07H 17/02
[52] U.S. Cl. ................... 514/25; 536/4.1; 536/17.2; 536/18.1; 536/122
[58] Field of Search ........ 536/4.1, 18.1, 122, 536/17.2; 519/25

[56] References Cited

U.S. PATENT DOCUMENTS

| | | | |
|---|---|---|---|
| Re. 30,354 | 7/1980 | Gordon | 536/4 |
| Re. 30,379 | 8/1980 | Gordon | 536/4 |
| Re. 32,268 | 10/1986 | Gordon | 514/25 |
| Re. 33,000 | 7/1989 | Gordon | 514/25 |
| 2,715,121 | 8/1955 | Glen et al. | 260/209 |
| 3,939,145 | 2/1976 | Gordon | 260/210 |
| 3,939,146 | 2/1976 | Gordon | 260/210 |
| 3,965,262 | 6/1976 | Gordon | 424/180 |
| 4,016,261 | 4/1977 | Gordon | 424/180 |
| 4,017,608 | 4/1977 | Gordon | 424/180 |
| 4,056,322 | 11/1977 | Gordon et al. | 536/4 |
| 4,251,520 | 2/1988 | Bruzzese et al. | 424/180 |
| 4,735,934 | 4/1988 | Gordon | 514/25 |
| 4,738,953 | 4/1988 | Gordon | 514/25 |
| 4,996,195 | 2/1991 | Ronsen et al. | 514/23 |
| 5,010,058 | 4/1991 | Ronsen et al. | 514/23 |
| 5,157,024 | 10/1992 | Gordon | 514/23 |
| 5,360,794 | 11/1994 | Arora | 514/25 |
| 5,367,062 | 11/1994 | Arora | 514/25 |

FOREIGN PATENT DOCUMENTS

| | | |
|---|---|---|
| WO92/04359 | 3/1992 | WIPO |
| WO92/14745 | 9/1992 | WIPO |
| WO93/13117 | 7/1993 | WIPO |

OTHER PUBLICATIONS

Z. Ahmed et al., Synthetic Communications, 18(5), 501–505, (1988).

*Primary Examiner*—Douglas W. Robinson
*Assistant Examiner*—Elli Peselev
*Attorney, Agent, or Firm*—Finnegan, Henderson, Farabow, Garrett & Dunner

[57] ABSTRACT

Compounds of this invention are derivatives of pentose monosaccharides which exhibit anti-proliferative and anti-inflammatory activity as well as intermediates for the synthesis of these compounds. Methods of preparation, pharmaceutical compositions containing the compounds and methods of treating inflammatory and/or autoimmune disorders employing the compounds are disclosed.

22 Claims, No Drawings

ANTI-PROLIFERATIVE AND ANTI-INFLAMMATORY COMPOUNDS: DERIVATIVES OF PENTOSE MONOSACCHARIDES

FIELD OF THE INVENTION

This invention relates to derivatives of pentose monosaccharides which exhibit anti-proliferative and anti-inflammatory activity as well as intermediate for the synthesis of these compounds. Compounds of the invention are useful for treating mammals with inflammatory and/or autoimmune disorders. This invention also relates to pharmaceutical compositions containing the disclosed compounds and to methods of treating inflammatory and/or autoimmune disorders employing the disclosed compounds.

DESCRIPTION OF THE RELATED ART

Certain monosaccharides and their derivatives are known to have therapeutic value in the treatment of inflammatory and autoimmune disorders. Monosaccharides, particularly the pentoses and hexoses, are well known compounds. Synthesis of derivatives of these sugars can generally be accomplished by synthetic techniques which are known in the art.

To prepare derivatives of the monosaccharides, it is common to block or protect one or more of the hydroxyl groups with acetal blocking groups such as isopropylidene or cyclohexylidene groups and leave only one or two hydroxyl groups free to undergo further reaction. Various blocking groups and methods are described in U.S. Pat. Nos. 2,715,121 and 4,056,322 and the disclosures of these patents are incorporated here by reference. For example, to prepare a derivative of $\alpha$,D-glucose which is blocked in its furanose ring structure, the 1,2- and 5,6-hydroxyl groups can be blocked using an isopropylidene blocking group and the 3-position left open to undergo further reaction. After the reaction to derivatize the 3-position is complete, the blocking groups may be selectively removed to allow for further derivatization at other positions if desired.

Various derivatives of monosaccharides, as well as synthetic methods for their preparation, are described in U.S. Pat. Nos. Re. 30,354, 30,379, 32,268, U.S. Pat. Nos. 4,056,322, 4,735,934, 4,738,953, 4,996,195 and 5,010,058. The therapeutic activity of various monosaccharides and their derivatives is also disclosed in the above documents. The disclosures of these documents are incorporated here by reference.

Two well known derivatives of $\alpha$,D-glucose having beneficial therapeutic properties are amiprilose, 1,2-O-Isopropylidene-3-O-3'-(N,N'-dimethylamino-n-propyl)-$\alpha$,D-glucofuranose, and its hydrochloric acid salt, amiprilose HCl (THERAFECTIN®). These compounds are known to have anti-inflammatory activity and demonstrate utility in managing the signs and symptoms of rheumatoid arthritis. More generally, these compounds have activity as immunomodulators, and therefore have a therapeutic effect on other autoimmune disorders such as psoriasis, eczema or lupus.

Deoxy derivatives of 1,2-O-Isopropylidene-$\alpha$,D-glucofuranose are described in U.S. Pat. No. 5,010,058. That patent describes methods of preparing deoxy derivatives of 1,2-O-Isopropylidene-$\alpha$,D-glucofuranose, and the use of such compounds in treating mammals with inflammatory and/or autoimmune disorders.

While some prior art monosaccharide derivatives have shown beneficial therapeutic activity, high doses of these monosaccharides may often be needed to be effective and produce the desired results. Because therapy for those inflammatory and autoimmune disorders is often chronic, there is a need to develop potent, non-toxic compounds which can be orally administered to promote ease of treatment and patient compliance.

An object of the present invention, therefore, is to provide new compounds that exhibit greater potency than available compounds.

Another object of the present invention is to provide a method of treating an animal or human suffering from an inflammatory and/or autoimmune disorder.

Other objects and advantages of the invention will be set forth in the description which follows, and in part will be apparent from the description, or may be learned by practice of the invention. The objects and advantages of the invention may be realized and obtained by means of the compounds, pharmaceutical compositions and methods of treatment set out in the appended claims.

SUMMARY OF THE INVENTION

To achieve the above objects, and in accordance with the purpose of the invention as embodied and broadly described here, there is provided:

A pentose monosaccharide compound of the formula I:

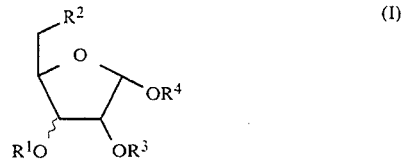

wherein
$R^1$ is $C_5$–$C_{15}$alkyl;
$R^2$ is a leaving group, NHR, $NH(CH_2)_mCH(Q)(CH_2)_pNR'R''$, or $O(CH_2)_mCH(Q)(CH_2)_pNR'R''$, wherein R is $C_3$–$C_8$alkyl, $C_3$–$C_8$hydroxyalkyl, cyclohexyl-$C_1$–$C_5$-alkyl, phenyl-$C_2$–$C_5$-alkyl or pyridinyl-$C_1$–$C_5$-alkyl, Q is H, $CH_3$, or $C_2H_5$, and m is from 1–4 and p is from 0–4 or Q is OH and m and p are from 1–3, R' and R" are each H or a lower alkyl group or, together with the nitrogen atom carrying them, form a saturated heterocyclic substituent of the formula:

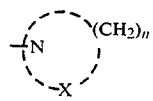

where X is $CH_2$, NH or O, and n ranges from 3–6, or $R^2$ is a saturated heterocyclic ring of the formula:

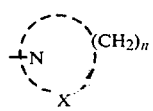

where X is CH$_2$, NH or O, and n is from 3–6; and R$^3$ and R$^4$ together form an acetal protecting group, or a physiologically acceptable salt thereof.

A compound of formula II:

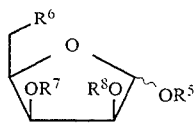  (II)

wherein
R$^5$ is C$_5$–C$_{15}$alkyl;
R$^6$ is leaving group, NHR, NH(CH$_2$)$_m$CH(Q)(CH$_2$)$_p$NR'R", or O(CH$_2$)$_m$CH(Q)(CH$_2$)$_p$NR'R", wherein R is C$_3$–C$_8$alkyl, C$_3$–C$_8$hydroxyalkyl, cyclohexyl-C$_1$–C$_5$-alkyl, phenyl-C$_2$–C$_5$-alkyl or pyridinyl-C$_1$–C$_5$-alkyl, Q is H, CH$_3$, or C$_2$H$_5$, and m is from 1–4 and p is from 0–4 or Q is OH and m and p are from 1–3, R' and R" are each H or a lower alkyl group or, together with the nitrogen atom carrying them, form a saturated heterocyclic substituent of the formula:

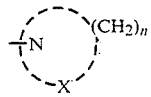

where X is CH$_2$, or O, and n ranges from 3–6, or R$^6$ is a saturated heterocyclic ring of the formula:

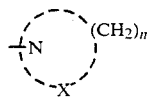

where X is CH$_2$, NH or O, and n is from 3–6; and
R$^7$ and R$^8$ together form an acetal protecting group, or a physiologically acceptable salt thereof.

The anti-proliferative and/or anti-inflammatory compounds according to the invention exhibit beneficial therapeutic properties and are useful in the treatment of inflammatory and autoimmune disorders. Specifically, these compounds have demonstrated inhibitory effects on lymphocyte proliferation and immunomodulatory activity in art recognized in vitro screening tests. Compounds having this activity are useful for treating animals and humans with various dermatological and/or arthritic conditions such as psoriasis, atopic dermatitis, rheumatoid arthritis, osteoarthritis, scleroderma and systemic lupus erythematosus.

The present invention also provides pharmaceutical compositions containing the subject pentose monosaccharide compounds, and methods for the treatment of inflammatory and/or autoimmune disorders employing those compounds. The pharmaceutical compositions comprise an effective amount of at least one of the subject compounds or a physiologically acceptable salt thereof with a pharmaceutically acceptable carrier.

Advantageously, the compounds of the present invention exhibit greater potency, in terms of their activity, than other known monosaccharides.

DETAILED DESCRIPTION OF THE INVENTION

In one embodiment of the invention, the pentose monosaccharides are represented by formula I:

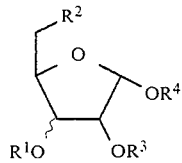  (I)

or physiologically acceptable salts thereof.

The substituent R$^1$ is a C$_5$–C$_{15}$alkyl group. An alkyl group according to and throughout this invention includes both straight chain and branched alkyl groups. Preferred C$_5$–C$_{15}$alkyl groups The substituent R$^2$ is a leaving group, NHR, NH(CH$_2$)$_m$CH(Q)(CH$_2$)$_p$NR'R", O(CH$_2$)$_m$CH(Q)(CH$_2$)$_p$NR'R", or a saturated heterocyclic substituent of the formula:

As intermediates in the preparation of the anti-proliferative and/or anti-inflammatory compounds of formula I, R$^2$ can be a leaving group such as Br or an oxygen-containing leaving group (O-leaving group) such as p-methylbenzenesulfonate (tosylate), P-bromobenzenesulfonate (brosylate), p-nitrobenzenesulfonate (nosylate), methylsulfonate (mesylate), or trifluoromethylsulfonate (triflate). A preferred leaving group is P-methylbenzenesulfonate. These leaving group derivatized compounds can be prepared by means known in the art.

When R$^2$ is NHR, the substituent R is C$_3$–C$_8$alkyl, C$_3$–C$_8$hydroxyalkyl, cyclohexyl-C$_1$–C$_5$-alkyl, phenyl-C$_2$–C$_5$-alkyl or pyridinyl-C$_1$–C$_5$-alkyl. Preferred C$_3$–C$_8$alkyl groups are butyl, hydroxypropyl and hydroxypentyl. A preferred cyclohexyl-C$_1$–C$_5$hexyl and heptyl. Preferred C$_3$–C$_8$hydroxyalkyl groups are alkyl group is methylcyclohexyl. A preferred phenyl-C$_2$–C$_5$-alkyl group is propylphenyl. A preferred pyridinyl-C$_1$–C$_5$-alkyl group is methylpyridinyl.

When R$^2$ is a NH(CH$_2$)$_m$CH(Q) (CH$_2$)$_p$NR'R" or a O(CH$_2$)$_m$CH(Q)(CH$_2$)$_p$NR'R" group, Q is H, CH$_3$, or C$_2$H$_5$, and m is from 1–4 and p is from 0–4, or Q is OH and m and p are from 1–3. Preferably, when Q is H or CH$_3$, m and p are 1 or 2 and when Q is OH, m and p are 1 or 2. Most preferably Q is H and m and p are 1. R' and R" are each H or a lower (C$_1$–C$_6$) alkyl group or, together with the nitrogen atom carrying them, form a saturated heterocyclic substituent of the formula:

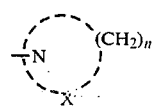

where X is CH$_2$, NH or O; and n ranges from 3–6. R' and R" are preferably each selected from H, methyl, ethyl, propyl or isopropyl and of these, most preferably, R' and R" are both methyl. Where R' and R", together with the nitrogen carrying them, form a heterocyclic substituent, the preferred substituents are selected from a pyrrolidinyl ring, a piperidinyl ring, and a morpholinyl ring.

As indicated above, the substituent $R^2$ may also be a saturated heterocyclic ring of the formula:

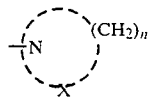

where X is $CH_2$, NH or O; and n ranges from 3-6. Preferred heterocyclic rings are selected from a pyrrolidinyl ring, a piperidinyl ring, and a morpholinyl ring.

The substituents $R^3$ and $R^4$ together form an acetal protecting group. Preferred acetal protecting groups include an Isopropylidene group and cyclohexylidene group.

The pentose monosaccharides of formula I include xylose derivatives and ribose derivatives. The following are preferred anti-proliferative and/or anti-inflammatory compounds:

1,2-O-Isopropylidene-3-O-heptyl-5-O-3'-(N',N'-dimethylaminopropyl)-α,D-xylofuranose, (Ia);

1,2-O-Isopropylidene-3-O-heptyl-5-deoxy-5-aminoheptyl-α,D-xylofuranose, (Ib);

1,2-O-Isopropylidene-3-O-heptyl-5-deoxy-5-N-3'-(N',N'-dimethyiaminopropyl)-α,D-xylofuranose, (Ic);

1,2-O-Isopropylidene-3-O-dodecyl-5-O-3'-(N',N'-dimethylaminopropyl)-α,D-xylofuranose, (Id);

1,2-O-Isopropylidene-3-O-dodecyl-5-deoxy-5-pyrolidinyl-α,D-xylofuranose, (Ie);

1,2-O-Isopropylidene-3-O-dodecyl-5-deoxy-5-N-3'-(N',N'-dimethylaminopropyl)-α,D-xylofuranose, (If);

1,2-O-Isopropylidene-3-O-decyl-5-O-3'-(N',N'-dimethylaminopropyl)-α,D-xylofuranose, (Ig);

1,2-O-Isopropylidene-3-O-decyl-5-deoxy-5-N-3'-(N',N'-dimethylaminopropyl)-α,D-xylofuranose, (Ih);

1,2-O-Isopropylidene-3-O-heptyl-5-deoxy-5-N-aminohexyl-α,D-xylofuranose, (Ii);

1,2-O-Isopropylidene-3-O-pentadecyl-5-O-3'-(N',N'-dimethylaminopropyl)-α,D-xylofuranose, (Ij);

1,2-O-Isopropylidene-3-O-pentadecyl-5-deoxy-5-aminopropylphenyl-α,D-xylofuranose, (Ik); 1,2-O-Isopropylidene-3-O-decyl-5-O-2'-(N',N'-Diisopropylaminoethyl)-α,D-xylofuranose, (Il);

1,2-O-Isopropylidene-3-O-decyl-5-O-3'-(N'-piperidinylpropyl)-α,D-xylofuranose, (Ira); and 1,2-O-Isopropylidene-3-O-heptyl-5-deoxy-5-pyrrolidinyl-α,D-xylofuranose, (In).

Particularly preferred compounds are compounds (Ia) and (Ih).

A second embodiment of this invention are pentose monosaccharide compounds of formula II:

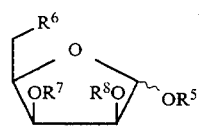

(II)

or physiologically acceptable salts thereof.

The substituent $R^5$ is $C_5$-$C_{15}$alkyl. $R^5$ has the same preferred embodiments as described above for $R^1$ in formula I.

The substituent $R^6$ is a leaving group, NHR, $NH(CH_2)_mCH(Q)(CH_2)_pNR'R''$, $O(CH_2)_mCH(Q)(CH_2)_pNR'R''$, or a saturated heterocyclic substituent of the formula:

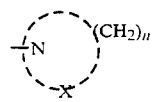

As intermediates in the preparation of the anti-proliferative and/or anti-inflammatory compounds of formula II, $R^6$ can be a leaving group such as Br or an oxygen-containing leaving group (O-leaving group) such as p-methylbenzenesulfonate (tosylate), p-bromobenzenesulfonate (brosylate), p-nitrobenzenesulfonate (nosylate), methylsulfonate (mesylate), or trifluoromethylsulfonate (triflate). A preferred leaving group is p-methylbenzenesulfonate. These leaving group derivatized compounds can be prepared by means known in the art.

When $R^6$ is NHR, the substituent R is $C_3$-$C_8$alkyl, $C_3$-$C_8$hydroxyalkyl, cyclohexyl-$C_1$-$C_5$-alkyl, phenyl-$C_2$-$C_5$-alkyl or pyridinyl-$C_1$-$C_5$-alkyl. Preferred $C_3$-$C_8$alkyl groups are butyl, hexyl and heptyl. Preferred $C_3$-$C_8$hydroxyalkyl groups are hydroxypropyl and hydroxypentyl. A preferred cyclohexyl-$C_1$-$C_5$alkyl group is methylcyclohexyl. A preferred phenyl-$C_2$-$C_5$-alkyl group is propylphenyl. A preferred pyridinyl-$C_1$-$C_5$-alkyl group is methylpyridinyl.

When $R^6$ is a $NH(CH_2)_mCH(Q)(CH_2)_pNR'R''$ or a $O(CH_2)_mCH(Q)(CH_2)_pNR'R''$ group, Q is H, $CH_3$, or $C_2H_5$, and m is from 1-4 and p is from 0-4 or Q is OH and m and p are from 1-3. Preferably when Q is H or $CH_3$, m and p are 1 or 2 and when Q is OH, m and p are 1-2. Most preferably Q is H and m and p are 1. R' and R" are each H or a lower ($C_1$-$C_6$) alkyl group or, together with the nitrogen atom carrying them, form a saturated heterocyclic substituent of the formula:

where X is $CH_2$, NH or O; and n ranges from 3-6. R' and R" are preferably each selected from H, methyl, ethyl, propyl or isopropyl and of these, most preferably, R' and R" are both methyl. Where R' and R", together with the nitrogen carrying them, form a heterocyclic substituent, the preferred substituents are selected from a pyrrolidinyl ring, a piperidinyl ring, and a morpholinyl ring.

The substituent $R^6$ may also be a saturated heterocyclic ring of the formula:

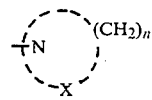

where X is $CH_2$, NH or O; and n ranges from 3-6. Preferred heterocyclic rings are selected from a pyrrolidinyl ring, a piperidinyl ring, and a morpholinyl ring.

The substituents $R^7$ and $R^8$ together form an acetal protecting group, preferably an isopropylidene or a cyclohexylidene group.

The pentose monosaccharides of formula II are derivatives of the monosaccharide lyxose and include both $\alpha$ and $\beta$ isomers. The following compounds are preferred:

Undecyl 2,3-O-Isopropylidene-5-deoxy-5-pyrrolidinyl-$\alpha$,D-lyxofuranose, (IIa); and Undecyl 2,3-O-Isopropylidene-5-deoxy-5-aminobutyl-$\alpha$,D-lyxofuranose, (IIb).

The anti-proliferative and/or anti-inflammatory compounds of the present invention also include the physiologically acceptable salts of the compounds of formulas I and II. Preferred physiologically acceptable salts are acid-addition salts. Common physiologically acceptable acid-addition salts are hydrochloric acid salts, oxalate salts and tartrate salts.

The compounds of the invention may be prepared according to the following general synthetic procedure. A suitably protected hexofuranose having a single free hydroxyl group is alkylated at that hydroxyl group using a base and an appropriate alkyl halide. Selective removal of a protecting group yields a 1,2-diol functionality which can be oxidatively cleaved to yield an alkylated pentofuranose derivative. Upon treatment of this pentofuranose derivative with a reducing agent a new pentofuranose is obtained that contains a free hydroxyl group. The free hydroxyl group can be alkylated with an appropriate alkyl halide and a base to give compounds of the present invention. Alternatively, the free hydroxyl group can also be derivatized to form a suitable leaving group such as tosylate and then the leaving group of the resulting derivative displaced with an amine to yield the deoxy, N-substituted compounds of the present invention. The examples below demonstrate this procedure, as well as the specific preparation, for compounds according to this invention. The examples are illustrative, and are not intended to limit, in any manner, the claimed invention.

Pharmacologic Activity

Compounds of the present invention have demonstrated immunomodulatory and anti-proliferative effects in biological assays. Standard in vitro immunologic assays were performed on compounds of the present invention in order to assess anti-proliferative and immunomodulatory activity. These included the mixed lymphocyte response (MLR), and the mouse spleen cell mitogen induced blastogenesis assay. The MLR functions as a test of immunomodulatory effects of the compounds whereby inhibitory effects on T lymphocyte activation and antigen presentation are determined. Anti-proliferative effects were demonstrated by measuring the inhibitory effects of compounds of present invention on the cellular proliferation of Concanavalin A stimulated murine splenocytes. Because inflammation and mechanisms involved in the pathogenesis of autoimmune diseases involve cellular activation and proliferation as well as abnormal immune system activation, these assays are appropriate to use as screens for novel compounds in the treatment of inflammatory and/or autoimmune disorders.

Compounds of the present invention demonstrated anti-proliferative and immunomodulatory activities. Concentrations tested ranged from 3 to 300 micromolar. With strong activity defined as half maximal inhibitory concentrations of less than 30 micromolar, compounds of the present invention uniformly demonstrated strong in vitro anti-proliferative effects. Similarly, compounds of this invention were also found to be strong immunomodulators. These results indicate that compounds of the present invention are extremely highly active agents with potent in vitro activities.

Pentose monosaccharide derivatives according to the present invention are useful for treating animals and mammals with inflammatory and/or autoimmune disorders such as psoriasis, atopic dermatitis, rheumatoid arthritis, osteoarthritis, scleroderma and systemic lupus erythematosus. Due to their valuable pharmacological properties, compounds of the present invention or their physiologically acceptable salts are particularly suitable for use as active compounds in pharmaceutical compositions for the treatment of, for example, rheumatic inflammatory disorders.

The anti-proliferative and/or anti-inflammatory compounds can either be administered alone in the form of microcapsules, in mixtures with one another or in combination with acceptable pharmaceutical carriers. The invention, thus, also relates to pharmaceutical compositions which comprise an effective amount of at least one compound of the present invention with or without a pharmaceutically and physiologically acceptable carrier. If appropriate, the compound may be administered in the form of a physiologically acceptable salt, for example, an acid-addition salt.

The present invention also encompasses a method of treating animals or humans suffering from inflammatory and/or autoimmune disorders which comprises administering to the animal or person an effective amount of at least one of the compounds of the invention, or an acid-addition salt thereof, with or without a pharmaceutically acceptable carrier. The compounds according to the invention can be administered orally, topically, rectally, anterally, internally, by boluses or, if desired, parenterally; oral administration is preferred.

Suitable solid or liquid galenic formulations are, for example, granules, powders, coated tablets, microcapsules, suppositories, syrups, elixirs, suspensions, emulsions, drops or injectable solutions. Also, compounds of the invention may be employed in preparations having a protracted release of the active compound. Commonly used additives in protracted release preparations are excipients, disintegrates, binders, coating agents, swelling agents, glidants, or lubricants, flavors, sweeteners or solubilizers. More specifically, frequently used additives are, for example, magnesium carbonate, titanium dioxide, lactose, mannitol and other sugars, talc, lactalbumin, gelatin, starch, cellulose and its derivatives, animal and vegetable oils, polyethylene glycols and solvents. The solvents include sterile water and monohydric or polyhydric alcohols such as glycerol.

The pharmaceutical compositions are preferably produced and administered in dosage units, each unit containing as an active component an effective dose of at least one compound of the present invention and/or at least one of its physiologically acceptable salts. In the case of mammals, the effective dose to treat autoimmune and/or anti-inflammatory disorders can range from about 1 to 100 mg per kilogram of body weight per day.

EXAMPLES

NMR spectra were recorded on a Varian XL-300 MHz using TMS as the internal standard reference. FTIR spectra were recorded on a Nicolet MX-1 instrument using KBr plates. Optical rotation was measured on a Perkin-Elmer Model 241 polarimeter. CIMS were obtained with a Finnigan MAT 4510 mass spectrometer with an INCOS data system. Generally, a direct exposure probe was used and ammonia or methane was used as a reagent gas (0.35 mm Hg, 120° C. source temperature).

EXAMPLE 1

1,2-O-Isopropylidene-3-O-heptyl-5-pyrrolidinyl-5-deoxy-α,D-xylofuranose.

Step 1: Preparation of 1,2-O-Isopropylidene-3-O-heptyl-α,D-glucofuranose.

The general procedure for the synthesis of 1,2-O-Isopropylidene-3-O-alkyl-α,D-glucofuranose (alkyl =has been described in U.S. Pat. No. 5,010,058.

Step 2: Preparation of 1,2-O-Isopropylidene-3-O-heptyl-α,D-xylofuranose.

1,2-O-Isopropylidene-3-O-heptyl-α,D-glucofuranose from step 1 (31.8 g) was dissolved in 60 ml of aqueous p-dioxane (50% v/v) at ambient temperature. To this was added dropwise an aqueous solution of sodium periodate (21.4 g in 175 ml). After 1.5 hours the reaction was judged to be complete by tlc. The solvent was removed under reduced pressure with mild heating. The solid obtained was triturated with dichloromethane (3×150 ml), the dichloromethane solutions were combined, dried over MgSO4, filtered and concentrated. The oil obtained (28.0 g, 97%) was used without further purification.

The oil obtained above (28 g) was dissolved in aqueous ethanol (500 ml, 75% v/v) at ambient temperature. To this was added dropwise an ethanolic solution of sodium borohydride (14.0 g in 200 ml). After 1 hour, the reaction was judged to be complete by tlc and the solvent was removed under reduced pressure. The resulting slurry was extracted with dichloromethane (3×200 ml). The combined extracts were dried over MgSO4, filtered, and concentrated. The crude product was chromatographed on silica gel (25% diethyl ether in hexanes) to give the desired 1,2-O-Isopropylidene-3-O-heptyl-α,D-xylofuranose in 92% overall yield.

Step 3: Preparation of 1,2-O-Isopropylidene-3-O-heptyl-5-O-P-tosyl-α,D-xylofuranose.

To a solution of 1,2-O-Isopropylidene-3-O-heptyl-5-O-p-tosyl-α,D-xylofuranose

To a solution of 1,2-O-Isopropylidene-3-O-heptyl-α,D-xylofuranose from step 2 (22.0 g) in pyridine (30 ml) was added a solution of tosylchloride (17.4 g) in pyridine (20 ml). The reaction mixture was stirred at room temperature and the reaction's progress monitored by tlc. After 4 hours the reaction mixture was concentrated, dissolved in ether, washed with aqueous sodium bicarbonate then water, dried over MgSO4, filtered and concentrated. The crude material obtained was chromatographed on silica gel (10% diethyl ether in hexanes) to give 1,2-O-Isopropylidene-3-O-heptyl-5-O-p-tosyl-α,D-xylofuranose (28.8 g).

Step 4: Preparation of 1,2-O-Isopropylidene-3-O-heptyl-5-deoxy-5-pyrrolidinyl-α,D-xylofuranose.

A mixture of 1,2-O-Isopropylidene-3-O-heptyl-5-O-p-tosyl-α,D-xylofuranose from step 3 (3.3 g) and pyrrolidine (3.0 g) was heated at 70°-80° C. After 1.5 hours the excess pyrrolidine was removed under reduced pressure. The residue was dissolved in diethyl ether and washed with a saturated sodium bicarbonate solution, a saturated brine solution, dried over MgSO4, filtered and concentrated. The crude material thus obtained was chromatographed on silica gel (30% diethyl ether in hexanes) to give 1,2-O-Isopropylidene-3-O-heptyl-5-deoxy-5-pyrrolidinyl-α,R-xylofuranose (2.0 g).

Other 3-O-alkyl derivatives such as decyl, dodecyl, pentadecyl, and derivatives were prepared according to the above procedure. The starting materials for step 1 were prepared by substituting an appropriate alkylhalide for the 1-bromoheptane employed in U.S. Pat. No. 5,010,058. Other 5-deoxy, 5-N derivatives were prepared by substituting an appropriate amine or diamine for pyrrolidine.

EXAMPLE 2

1,2-O-Isopropylidene-3-O-heptyl-5-O-Dimethylaminopropyl-α,D-xylofuranose.

This material was prepared by treating 1,2-O-Isopropylidene-3-O-heptyl-α,D-xylofuranose (Example 1, Step 2) with powdered sodium hydroxide and dimethylaminopropyl chloride according to the procedure in Example 3, Step 1 of U.S. Pat. No. 5,010,058. The title compound was obtained in 59% yield after chromatography on silica gel (5% diethyl ether in hexanes to 100% diethyl ether). Other 3-O-alkyl derivatives such as decyl, dodecyl, and pentadecyl derivatives were prepared by substituting an appropriate alkylhalide for the 1-bromoheptane employed here. Other 5-0 derivatives were prepared by substituting an appropriate aminoalkyl halide for the dimethylaminopropyl chloride.

EXAMPLE 3

Undecyl 2,3-O-Isopropylidene-5-deoxy-5-pyrrolidinyl-α,D-lyxofuranose.

Step 1: Preparation of Undecyl 2,3:5,6-O-DiIsopropylidene-α,D-Mannofuranoside.

Sodium hydride (2.2 g) was added to a solution of 2,3:5,6-Di-O-Isopropylidene-α,D-mannofuranose (20 g) and undecyl bromide (21 g) in anhydrous DMF (50 ml). The reaction mixture was warmed to 35° C. until tlc indicated no presence of starting material. The reaction was quenched by the addition of methanol (20 ml) and then water (10 ml). The reaction mixture was concentrated under reduced pressure and the residue obtained dissolved in diethylether. The ether solution was washed with water (2×50 ml) and saturated sodium chloride solution (30 ml), dried over MgSO4, filtered and concentrated. The crude material thus obtained was purified by silica gel chromatography (10% ether in hexanes) to give the title compound (14.0 g).

Step 2: Preparation of Undecyl 2,3-O-Isopropylidene-α,D-mannofuranoside.

To a solution of undecyl 2,3:5,6-O-diisopropylidene-α,D-mannofuranoside (11.5 g) in THF (12 ml), cooled to 5° C. odecylice-water bath, was added dropwise a 30% HClO₄ solution (11.5 ml). The reaction mixture was stirred and monitored by tlc. After 2 hrs a further 10 ml of 30% HClO₄ was added. Upon complete consumption of the starting material, as judged by tlc, the reaction mixture was quenched with a saturated aqueous K₂CO₃ solution, filtered and concentrated under reduced pressure. The residue obtained was dissolved in diethylether, dried over MgSO₄, filtered, concentrated and chromatographed on silica gel with 1:1 ether hexanes to give the title compound (4 g).

Step 3: Preparation of Undecyl 2,3-O-Isopropylidene-α,D-lyxofuranoside.

To a 1:1 dioxane/water (10 ml) solution of Undecyl 2,3-O-Isopropylidene-α,D-mannofuranoside (5 g) was added an aqueous solution of sodium periodate (2.9 g dissolved in 60 ml H₂O). After stirring 4 hrs at room temperature the reaction was judged to be complete by tlc. The reaction mixture was concentrated under reduced pressure and the residue obtained triturated three times with dichloromethane. The organic fractions were combined, dried over MgSO₄, filtered and concentrated. The material obtained was carried forward without further purification.

The material obtained above (3.9 g) was dissolved in 75% ethanol in water (80 ml). To this was added, dropwise, a solution of sodium borohydride (2.6 g) in ethanol (70 ml). The reaction mixture was stirred at room temperature for approximately 4 hrs at which time there was no trace of starting material by tlc. The solvent was removed under reduced pressure, and the resulting slurry extracted with dichloromethane. The dichloromethane extracts were combined, dried over MgSO₄, filtered and concentrated. The crude product obtained was chromatographed on silica gel (30% diethyl ether in hexane) to give the title compound (2 g).

Step 4: Preparation of Undecyl 2,3-O-Isopropylidene-5-deoxy-5-pyrrolidinyl-α,D-lyxofuranoside.

To a solution of undecyl 2,3-O-Isopropylidene-,lyxofuranoside (2 g) in pyridine (5 ml) was added tosylchloride (1.4 g) dissolved in pyridine (5 ml). The resulting mixture was stirred at room temperature and the reaction monitored by tlc. Upon disappearance of starting material the reaction mixture was concentrated, dissolved in ether, washed with aqueous solution bicarbonate then with water, dried over MgSO₄, filtered and concentrated. The crude material obtained was chromatographed on silica gel (10% diethyl ether in hexanes) to give undecyl 2,3-O-Isopropylidene-5-p-tosyl-α,D-lyxofuranoside.

A mixture of undecyl 1,2-O-Isopropylidene-5-p-tosyl-α,D-lyxofuranoside (1.0 g) and pyrrolidine (5 ml) was heated at 75° C. for 1 hr. The reaction mixture was concentrated under reduced pressure and the crude obtained was chromatographed on silica gel (diethyl ether as eluent). Undecyl 2,3-O-Isopropylidene-5-deoxy- 5-pyrrolidinyl-α,D-lyxofuranose was obtained as a pale yellow oil (0.5 g).

Other glycosides such as decyl were prepared by substituting decyl bromide for the undecyl bromide employed in the preparation of undecyl 2,3-O-Isopropylidene-,-mannofuranose. Additional compounds can be prepared by similarly substituting an appropriate C₅-C₁₅alkyl halide for the undecyl bromide and/or by substituting an appropriate amine or diamine for pyrrolidine.

The claimed invention is:

1. A xylose or ribose monosaccharide compound of the formula I:

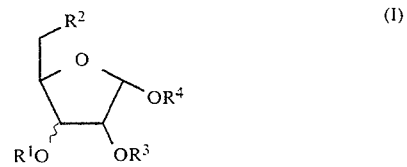

wherein
R¹ is C₅-C₁₅alkyl;
R² is NHR, NH(CH₂)$_m$CH(Q)(CH₂)$_p$NR'R", or O(CH₂)$_m$CH(Q)(CH₂)$_p$NR'R", wherein R is C₃-C₈alkyl, C₃-C₈hydroxyalkyl, cyclohexyl-C₁-C₅-alkyl, phenyl-C₂-C₅-alkyl or pyridinyl-C₁-C₅-alkyl, Q is H, CH₃, or C₂H₅, and m is from 1-4 and p is from 0-4 or Q is OH and m and p are from 1-3, R' and R" are each H or a lower alkyl group or, together with the nitrogen atom carrying them, form a saturated heterocyclic substituent of the formula:

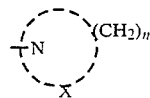

where X is CH₂, NH or O, and n ranges from 3-6, or R² is a saturated heterocyclic ring of the formula:

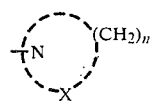

where X is CH₂, NH or O, and n is from 3-6; and
R³ and R⁴ together form an acetal protecting group selected from the group consisting of an isopropylidene group and a cyclohexylidene group, or a physiologically acceptable salt thereof.

2. The compound of claim 1, wherein
R¹ is heptyl, decyl, dodecyl, or pentadecyl,
R² is NHR, wherein R is butyl, hexyl, heptyl, hydroxypropyl or hydroxypentyl;
NH(CH₂)$_m$CH(Q)(CH₂)$_p$NR'R", or O(CH₂)$_m$CH(Q)(CH₂)$_p$NR'R", wherein Q is H, or CH₃ and m and p are 1 or 2 or Q is OH and m and p are 1 or 2, R' and R" are each selected from the group consisting of H, methyl, ethyl, propyl and isopropyl, or where R' and R", together with the nitrogen carrying them, form a heterocycle selected from the group consisting of a pyrrolidinyl ring, a piperidinyl ring, and a morpholinyl ring; or
said saturated heterocyclic substituent of the formula:

is selected from the group consisting of a pyrrolidinyl ring, a piperidinyl ring, and a morpholinyl ring; and R³ and R⁴ form an isopropylidene group or a physiologically acceptable salt thereof.

3. The compound of claim 2, wherein said compound is a xylose derivative.

4. The compound of claim 3, wherein said compound is selected from the group consisting of
1,2-O-Isopropylidene-3-O-heptyl-5-O-3'-(N',N'-dimethylaminopropyl)-α,D-xylofuranose,
1,2-O-Isopropylidene-3-O-heptyl-5-deoxy-5-aminoheptyl-α,D-xylofuranose,
1,2-O-Isopropylidene-3-O-heptyl-5-deoxy-5-N-3'-(N',N'-dimethylaminopropyl)-α,D-xylofuranose,
1,2-O-Isopropylidene-3-O-dodecyl-5-O-3'-(N',N'-dimethylaminopropyl)-α,D-xylofuranose,
1,2-O-Isopropylidene-3-O-dodecyl-5-deoxy-5-pyrolidinyl-α,D-xylofuranose,
1,2-O-Isopropylidene-3-O-dodecyl-5-deoxy-5-N'3'-(N',N'-dimethylaminopropyl)-α,D-xylofuranose,
1,2-O-Isopropylidene-3-O-decyl-5-O-3'-(N',N'-dimethylaminopropyl)-α,D-xylofuranose,
1,2-O-Isopropylidene-3-O-decyl-5-deoxy-5-N-3'-(N',N'-dimethylaminopropyl)-α,D-xylofuranose,
1,2-O-Isopropylidene-3-O-heptyl-5-deoxy-5-N-aminohexyl-α,D-xylofuranose,
1,2-O-Isopropylidene-3-O-pentadecyl-5-O-3'-(N',N'-dimethylaminopropyl)-α,D-xylofuranose,
1,2-O-Isopropylidene-3-O-pentadecyl-5-deoxy-5-aminopropylphenyl-α,D-xylofuranose,
1,2-O-Isopropylidene-3-O-decyl-5-O-2'-(N',N'-Diisopropylaminoethyl)-α,D-xylofuranose,
1,2-O-Isopropylidene-3-O-decyl-5-O-3'-(N'-piperidinylpropyl)-α,D-xylofuranose, and
1,2-O-Isopropylidene-3-O-heptyl-5-deoxy-5-pyrrolidinyl-α,D-xylofuranose.

5. The compound of claim 2 wherein said compound is 1,2-O- Isopropylidene-3-O-heptyl-5-O-3'(N,N'-dimethylaminopropyl)-α,D-xylofuranose.

6. The compound of claim 2 wherein said compound is 1,2-O-Isopropylidene-3-O-decyl-5-deoxy-5-N-3'-(N',N'-dimethylaminopropyl)-α,D-xylofuranose.

7. A pharmaceutical composition for the treatment of an inflammatory or an autoimmune disorder comprising a pharmaceutically effective amount of a compound according to claim 1 to treat the inflammatory or autoimmune disorder and a pharmaceutically acceptable carrier.

8. A method of treating an animal or human suffering from an inflammatory or autoimmune disorder comprising administering thereto an amount effective to treat an inflammatory or an autoimmune disorder of the compound according to claim 1.

9. A pharmaceutical composition for the treatment of an inflammatory or an autoimmune disorder comprising a pharmaceutically effective amount of a compound according to claim 2 to treat the inflammatory or autoimmune disorder and a pharmaceutically acceptable carrier.

10. A method of treating an animal or human suffering from an inflammatory or autoimmune disorder comprising administering thereto an amount effective to treat an inflammatory or an autoimmune disorder of the compound according to claim 2.

11. A pharmaceutical composition for the treatment of an inflammatory or an autoimmune disorder comprising a pharmaceutically effective amount of a compound according to claim 5 to treat the inflammatory or autoimmune disorder and a pharmaceutically acceptable carrier.

12. A method of treating an animal or human suffering from an inflammatory or autoimmune disorder comprising administering thereto an amount effective to treat an inflammatory or an autoimmune disorder of the compound according to claim 5.

13. A pharmaceutical composition for the treatment of an inflammatory or an autoimmune disorder comprising a pharmaceutically effective amount of a compound according to claim 6 to treat the inflammatory or autoimmune disorder and a pharmaceutically acceptable carrier.

14. A method of treating an animal or human suffering from an inflammatory or autoimmune disorder comprising administering thereto an amount effective to treat an inflammatory or an autoimmune disorder of the compound according to claim 6.

15. The pharmaceutical composition of claim 7, wherein the disorder is psoriasis, atopic dermatitis, rheumatoid arthritis, osteoarthritis, scleroderma or systemic lupus erythematosus.

16. The method of claim 8, wherein the disorder is psoriasis, atopic dermatitis, rheumatoid arthritis, osteoarthritis, scleroderma or systemic lupus erythematosus.

17. The pharmaceutical composition of claim 9, wherein the disorder is psoriasis, atopic dermatitis, rheumatoid arthritis, osteoarthritis, scleroderma or systemic lupus erythematosus.

18. The method of claim 10, wherein the disorder is psoriasis, atopic dermatitis, rheumatoid arthritis, osteoarthritis, scleroderma or systemic lupus erythematosus.

19. The pharmaceutical composition of claim 11, wherein the disorder is psoriasis, atopic dermatitis, rheumatoid arthritis, osteoarthritis, scleroderma or systemic lupus erythematosus.

20. The method of claim 12, wherein the disorder is psoriasis, atopic dermatitis, rheumatoid arthritis, osteoarthritis, scleroderma or systemic lupus erythematosus.

21. The pharmaceutical composition of claim 13, wherein the disorder is psoriasis, atopic dermatitis, rheumatoid arthritis, osteoarthritis, scleroderma or systemic lupus erythematosus.

22. The method of claim 14, wherein the disorder is psoriasis, atopic dermatitis, rheumatoid arthritis, osteoarthritis, scleroderma or systemic lupus erythematosus.

* * * * *

UNITED STATES PATENT AND TRADEMARK OFFICE
CERTIFICATE OF CORRECTION

PATENT NO. : 5,432,163

DATED : July 11, 1995

INVENTOR(S) : M. Nayeem Akhtar; David S. Thomson and Sudershan K. Arora

It is certified that error appears in the above-identified patent and that said Letters Patent is hereby corrected as shown below:

Claim 1, Col. 12, line 17, "$C_5$-$C_{15}$alkyl" should read --$C_5$-$C_{15}$ alkyl--;

lines 19-20, "$C_3$-$C_8$alkyl" should read --$C_3$-$C_8$ alkyl--;

line 20, "$C_3$-$C_8$hydroxyalkyl" should read --$C_3$-$C_8$ hydroxyalkyl--.

Claim 4, Col. 13, line 26, "N'3'" should read --N-3'--.

Signed and Sealed this

Nineteenth Day of September, 1995

Attest:

BRUCE LEHMAN

*Attesting Officer*  *Commissioner of Patents and Trademarks*